United States Patent
Yoshimatsu et al.

(10) Patent No.: US 6,995,199 B2
(45) Date of Patent: Feb. 7, 2006

(54) WOOD-BASED REFINED TAR-CONTAINING COATING COMPOSITIONS

(75) Inventors: Michiharu Yoshimatsu, Crescent Shin-Yokohama Ildomani 802, 1-29-11, Shin-yokohama, Kouhoku-ku, Yokohama-shi, Kanagawa (JP) 222-0033; Yuzuru Suetake, Tokyo (JP)

(73) Assignee: Michiharu Yoshimatsu, Yokohama (JP)

( * ) Notice: Subject to any disclaimer, the term of this patent is extended or adjusted under 35 U.S.C. 154(b) by 0 days.

(21) Appl. No.: 10/483,086

(22) PCT Filed: Jul. 8, 2002

(86) PCT No.: PCT/JP02/06897

§ 371 (c)(1),
(2), (4) Date: Jan. 8, 2004

(87) PCT Pub. No.: WO03/005826

PCT Pub. Date: Jan. 23, 2003

(65) Prior Publication Data

US 2004/0186204 A1    Sep. 23, 2004

(30) Foreign Application Priority Data

Jul. 10, 2001 (JP) .............................. 2001-209762

(51) Int. Cl.
*C08L 95/00* (2006.01)
(52) U.S. Cl. ...................................................... 524/60
(58) Field of Classification Search ............. 524/60–61
See application file for complete search history.

(56) References Cited

FOREIGN PATENT DOCUMENTS

| JP | 08-143401 | 6/1996 |
| JP | 2002-000093 | 1/2002 |
| JP | 2002-167306 | 6/2002 |
| WO | 99/48656 | 9/1999 |
| WO | 00/02716 | 1/2000 |

OTHER PUBLICATIONS

Brossard, P.L.E., et al., Biomass and Bioenergy, vol. 12, No 5, pp. 363-366 (1997).
Chakma, A., et al., J. Can. Pet. Technol., vol. 32, No. 5, pp. 48-51 (1993)
Mikula, R.J., et al., Fuel Sci. Technol. Int., vol. 7, No. 5-6, pp. 727-749, (1989).

*Primary Examiner*—Peter Szekely
(74) *Attorney, Agent, or Firm*—Wenderoth, Lind & Ponack, L.L.P.

(57) ABSTRACT

An aqueous tar solution having excellent stability in which tar is dissolved in a liquid and which does not cause precipitation or separation, as well as a tar-containing coating composition having highly rot- and termite-proofing effects, are provided. The aqueous tar solution is obtained by mixing 10 to 50 g of a 10–50% NaOH solution is mixed, relative to 100 g of tar, to produce a processed tar, and further mixing and dissolving 100 g of a 2–5% NaOH solution, relative to 10 to 20 g of the processed tar. The tar-containing coating composition is obtained by mixing the aqueous tar solution in an aqueous coating composition having resin as the major component and containing charcoal powder.

1 Claim, No Drawings

WOOD-BASED REFINED TAR-CONTAINING COATING COMPOSITIONS

TECHNICAL FIELD

The present invention relates to an aqueous tar solution and a tar-containing coating composition. More specifically, the present invention relates to an aqueous solution in which tar is dissolved in a liquid and which possesses excellent stability properties of causing neither precipitation nor separation, and to a tar-containing coating composition having highly rot-proofing and termite-controlling effects.

BACKGROUND ART

Until now, it is known that fumes generated during producing charcoal are separated into three layers within a container when cooled for the production of wood vinegar (pyroligneous acid) tar. That is, generated fumes are separated into three layers: (a) wood vinegar (aqueous), (b) tar and wood vinegar, and (c) tar (semisolid) from top to bottom within a container, since the wood vinegar is aqueous and the tar is not soluble in water and has a high specific gravity. The fraction (b) described above, in particular, is a mixture of tar and wood vinegar, and it is difficult to separate them completely.

In addition, tar is of oil, and does not result in complete dryness. For example, experiments in which tar was applied to plates with given dimensions, followed by allowing the plates to be placed in a dryer at about 60° C. for 60 days gave results from which it turned out that the tar was not dried completely and remained in a tacky (sticky) state at all times.

In order to avoid this disadvantage of incomplete drying of tar, attempts are possibly be made to dilute tar in a volatile solvent such as a lacquer thinner, alcohol, benzine, petroleum, or the like, followed by application of this diluted tar. In this case, however, the tar will remain in a tacky state and its complete dryness will be not achieved, as in the above-described experiments, after the solvent vaporizes.

As mentioned above, tar is not soluble in water and does not exist in a stable state in a liquid, and precipitation of tar components is caused, for example, during production and storage, thereby leading to disadvantage of separation into wood vinegar and tar. In addition, tar is not dried completely, and thus there is a disadvantage of causing it to remain in a sticky, tacky state in the case of applying it to plates and others.

Tar, on the other hand, has been known in the past to have rot-proofing and termite-controlling effects. Therefore, it can be expected that if tar is used as coatings to apply tar to lumbers and others, rot, damages by termites, and others can be prevented. Additionally, tar does not make human bodies and the environment dirty and has extremely high usefulness.

However, tar is not dissolved in a liquid in a stable state, and thus it is difficult to mix tar into coating compositions. Even if tar is applied to lumbers and others, the tar is not dried completely, and thus there are problems of precluding its use as coating compositions, due to attaching of tar in surrounding areas.

Therefore, the first object of the present invention is to provide an aqueous solution in which tar is dissolved in a stable state.

The second object of the present invention is to provide a tar-containing coating composition having highly rot-proofing and termite-controlling effects in which tar can be completely dried after being applied for coating.

DISCLOSURE OF INVENTION

In order to accomplish the first object mentioned above, the present invention provides an aqueous tar solution produced by mixing tar and an NaOH solution to be dissolved in each other.

More concretely, the present invention provides an aqueous tar solution produced by mixing 100 parts by weight of tar and 10 to 50 parts by weight of a 10–50% NaOH solution to prepare a processed tar, and mixing 100 parts by weight of a 2–5% NaOH solution and 10 to 20 parts by weight of the processed tar to be dissolved in each other. Thus, since tar is dissolved in an NaOH solution having a determined concentration so as to be uniformly dispersed in an aqueous solution, tar is permitted to exist in a stable state in the solution, which results in the formation of an aqueous tar solution that does not cause disadvantages such as precipitation, separation, and the like.

In order to accomplish the second object mentioned above, the present invention further provides a tar-containing coating composition produced by mixing an aqueous coating composition containing a resin as a main component and containing charcoal powder with an aqueous tar solution prepared by mixing a wood-based tar, zeolite and an NaOH solution to be dissolved in each other. Since tar is dissolved in a stable state in the aqueous coating composition, tar can be coated in a condition of being uniformly dispersed when the aqueous coating composition is applied to lumbers or the like, whereby rot-proofing and termite-controlling effects can be brought. Furthermore, the tar-containing coating composition can be expected to have humidity-conditioning and deodorizing effects of charcoal without adverse effects given on human bodies and without environmental pollution. Moreover, since tar dispersed in the coating composition is coated and dried as well as the resin contents in the composition, it brings a stable coated surface which does not soil when being touched on.

BEST MODE FOR CARRYING OUT THE INVENTION

Embodiments of aqueous tar solutions of the present invention for accomplishing the first object are now described on the basis of experimental examples.

As tar is not soluble in water, mixture of tar and water results in separation of a tar layer and an aqueous layer (wood vinegar) during production and preservation. Thus, based on the premise that the use of a surfactant can bring about some solution to the following purposes of the examinations as tar is considered to be of oil, the following examinations were carried-out first.

Purposes of Examinations:
1. To prevent precipitation and separation of tar and to produce a tar which has a stable viscosity.
2. To produce a tar which is soluble in water.

Examination 1:
  NaOH was employed as a surfactant.
  (1) In a beaker, 100 ml of tar was placed, and 10 g of granular NaOH was mixed therewith; and
  (2) In a beaker, 100 ml of tar was placed, and 50 ml of a 2% NaOH aqueous solution was mixed therewith.

Results of Examination 1:

Examination (1): The NaOH remained at the bottom of the beaker and was not dissolved immediately. Even after leaving it standing for ten days, complete dissolution was not achieved.

Examination (2): Complete dissolution was achieved.

Discussion:

It was observed that the complete dissolution was not achieved when tar was mixed with NaOH granules, whereas the tar was dissolved in the NaOH aqueous solution having a given concentration. The following examinations were carried out to determine the concentration, viscosity, and stability of processed tars to adapt tar to the purposes of its use and others.

Examination 2:

As indicated in (a) to (f) below, processed tars were prepared by adding 10 or 50 g of an NaOH aqueous solution having a given concentration to 100 g of tar.
  (a) 10 g of a 10% NaOH aqueous solution was mixed in 100 g of tar;
  (b) 10 g of a 25% NaOH aqueous solution was mixed in 100 g of tar;
  (c) 10 g of a 50% NaOH aqueous solution was mixed in 100 g of tar;
  (d) 50 g of a 10% NaOH aqueous solution was mixed in 100 g of tar;
  (e) 50 g of a 25% NaOH aqueous solution was mixed in 100 g of tar; and
  (f) 50 g of a 50% NaOH aqueous solution was mixed in 100 g of tar.

Results of Examination 2:

In all the above-described cases (a) to (f), the reaction heat was generated during mixing (about 22 to 26° C.). The viscosity of tar was slightly increased one hour after mixing and afterward, and at a subsequent time, the viscosity displayed a good stability. In addition, no change in viscosity determinations was observed even after the lapses of 30 days and 60 days, and the viscosity was stable. It was observed that processed tar (c) gave the highest stability above all.

Examination 3:

As indicated in (i) to (viii) below, given amounts of tar were mixed and dissolved in 100 g of NaOH solutions having given concentrations.
  (i) 10 g of the processed tar (c) from Examination 2 was mixed in 100 g of a 5% NaOH solution;
  (ii) 10 g of the processed tar (d) from Examination 2 was mixed in 100 g of a 5% NaOH solution;
  (iii) 10 g of the processed tar (e) from Examination 2 was mixed in 100 g of a 5% NaOH solution;
  (iv) 10 g of the processed tar (f) from Examination 2 was mixed in 100 g of a 5% NaOH solution;
  (v) 10 g of tar was mixed in 100 g of a 5% NaOH solution;
  (vi) 10 g of tar was mixed in 100 g of a 2% NaOH solution;
  (vii) 20 g of tar was mixed in 100 g of a 5% NaOH solution; and
  (viii) 20 g of tar was mixed in 100 g of a 2% NaOH solution.

Results of Examination 3:

In all the above-described cases (i) to (viii), it was observed that tar was dissolved. Furthermore, there was not caused any precipitation in the solutions after the lapses of 30 days and 60 days, and the stability was observed to be good.

Examination 4:

This examination was carried out to determine the stability by applying 10 g of each of the processed tars (a) to (f) from Examination 2 onto the center area of an aluminum plate (100 mm×100 mm). Aluminum plates onto which the processed tars were applied were placed and dried in a dryer at 60±2° C. for 48 hours.

Results of Examination 4:

In the case that the processed tar (c) of Experiment 2 was applied, the viscosity was increased, and the tar remained tacky and in a wet state, while a good stability was observed.

Summary of Examinations 1 to 4:

By mixing 10 to 50 g of a 10–50% NaOH aqueous solution in 100 g of tar, it was possible to solve instabilities due to precipitation and solidification which are problems with conventional tars, and to obtain processed tars having stable viscosities at normal temperature, properties causing neither precipitation nor solidification, and superior stability. It has been found that in particular, the processed tar (c) in which 10 g of a 50% NaOH aqueous solution was mixed in 100 g of tar is easy to use in terms of viscosity and the like, though the concentration and amount can be varied, depending on the purposes of its use and the like.

In addition, aqueous tar solutions causing neither precipitation nor solidification and having good stability were able to be obtained by mixing and dissolving 10 to 20 g of tar or a processed tar in 100 g of a 2–5% NaOH solution.

In other words, it has been found that tar can uniformly be dissolved using an NaOH aqueous solution having a given concentration to be stable in properties. Depending on mixing ratio by weight of tar to an NaOH aqueous solution having a given concentration, the mixing and dissolving is able to produce a processed tar having a high viscosity or an aqueous tar solution having a low viscosity which is to be used for being mixed with other materials.

Embodiments of tar-containing coating compositions of the present invention for accomplishing the second object are now described on the basis of experimental examples.

The tar-containing coating compositions of the present invention are those compositions produced by mixing an aqueous coating composition containing a resin (nylon or acrylic resin, etc.) as a major component and charcoal powder (hereinafter referred to as Health Coat (registered trade mark)) with an aqueous tar solution prepared by mixing and dissolving tar in an NaOH solution. Examples of examinations are described for improving Health Coat.

Purposes:
  1. To enhance properties against termite damage; and
  2. To enhance rot-proofing properties.

Discussion:

It was likely that enhancement of properties against termite damage and for rot proofing can be accomplished by mixing a wood-based tar. Examinations were carried out to determine effects by mixing tar in aqueous and alcoholic systems of Health Coat.

Examination 5:
  (1) 3 g of tar was mixed in 100 g of Health Coat (alcoholic);
  (2) 5 g of tar was mixed in 100 g of Health Coat (alcoholic);

(3) 7 g of tar was mixed in 100 g of Health Coat (alcoholic);
(4) 10 g of tar was mixed in 100 g of Health Coat (alcoholic);
(5) 3 g of tar was mixed in 100 g of Health Coat (aqueous);
(6) 5 g of tar was mixed in 100 g of Health Coat (aqueous);
(7) 7 g of tar was mixed in 100 g of Health Coat (aqueous); and
(8) 10 g of tar was mixed in 100 g of Health Coat (aqueous).

Results of Examination 5:

The cases (1) to (4) provided a good solubility of tar-without any problem. The cases (5) to (8) resulted in gelation, and could not be used.

Discussion:

Tar was dissolved in the alcoholic systems without any problem, but provided a poor compatibility with aqueous systems. In order to mix tar in the water-based Health Coat, it is necessary to determine the compatibility of each raw material of the water-based Health Coat with tar, and whether a water-soluble tar can be mixed.

Examination 6:

(1) 10 g of each of the following water-soluble tars (a) to (f) was mixed in 100 g of the water-based Health Coat.
 (a) 10 g of tar was mixed in 100 g of a 3% NaOH solution;
 (b) 10 g of tar was mixed in 100 g of a 5% NaOH solution;
 (c) 10 g of tar was mixed in 100 g of a 10% NaOH solution;
 (d) 10 g of tar was mixed in 100 g of a 15% NaOH solution;
 (e) 10 g of tar was mixed in 100 g of a 20% NaOH solution; and
 (f) 0 g of tar was mixed in 100 g of a 25% NaOH solution.

Results of Examination 6:

All of the cases using the water-soluble tar (a) to (f) resulted in gelation.

Examination 7:

The water-based Health Coat was separated into its raw materials, in each of which tar was mixed.
 (a) 3 g of tar was mixed in acrylic resin (hereinafter referred to as "AC"); and
 (b) 3 g of tar was mixed in 30 g of an aqueous nylon solution.

Results of Examination 7:

The case (a) resulted in gelation, whereas the case (b) was mixed to be dissolved.

Discussion:

Although it was likely that mixing of tar in AC requires a water-soluble tar, all the cases resulted in gelation in Examination 7. Next, effects were ascertained using tar treated with an aqueous solution of NaOH, as follows.

Examination 8:

(1) 10 g of a 50% NaOH aqueous solution was mixed in 100 g of tar; and
(2) 50 g of a 50% NaOH aqueous solution was mixed in 100 g of tar.
 (a) 3 g of the resultant of (1) in Examination 8 was mixed in 30 g of AC (acrylic resin);
 (b) 3 g of the resultant of (2) in Examination 8 was mixed in 30 g of AC (acrylic resin);
 (c) 3 g of the resultant of (1) in Examination 8 was mixed in 30 g of an aqueous nylon solution; and
 (d) 3 g of the resultant of (2) in Examination 8 was mixed in 30 g of an aqueous nylon solution.

Results of Examination 8:

The case (a) resulted in gelation of large granules. The case (b) resulted in gelation of small granules. The case (c) resulted in gelation of large granules. The case (d) resulted in gelation of large granules.

Discussion:

It was necessary to determine the compatibility of each of the AC and an aqueous nylon solution with the processed tar which was treated with NaOH.
 (1) A poor compatibility was observed between the AC and the tar.
 (2) A good compatibility was observed between the aqueous nylon solution and the tar.
 (3) A poor compatibility was observed between the AC and the processed tar treated with NaOH.
 (4) A poor compatibility was observed between the aqueous nylon solution and the processed tar treated with NaOH.

Taking into account the above-described results (1) to (4), it is necessary to determine the compatibility of each of the AC and the aqueous nylon solution with an NaOH solution.

Examination 9:

(1) 10 g of a 2% NaOH solution was mixed in 30 g of AC (acrylic resin).
(2) 10 g of a 2% NaOH solution was mixed in 30 g of an aqueous nylon solution.

Results of Examination 9:

The above-described experiment (1) resulted in the resultant being in a dissolved state, and the above-described experiment (2) resulted in the resultant being in a separated state.

Discussion:

A poor compatibility was observed between the aqueous nylon solution and the NaOH solution, and the processed tar treated with the NaOH solution was unusable.

Examination 10:

(1) A solution containing 100 g of a 1% NaOH solution and 10 g of tar was mixed with 100 g of AC (acrylic resin);
(2) A solution containing 100 g of a 2% NaOH solution and 10 g of tar was mixed with 100 g of AC;
(3) A solution containing 100 g of a 3% NaOH solution and 10 g of tar was mixed with 100 g of AC;
(4) A solution containing 100 g of a 4% NaOH solution and 10 g of tar was mixed with 100 g of AC;
(5) A solution containing 100 g of a 5% NaOH solution and 10 g of tar was mixed with 100 g of AC;
(6) A solution containing 100 g of a 1% NaOH solution and 50 g of tar was mixed with 100 g of AC;
(7) A solution containing 100 g of a 2% NaOH solution and 50 g of tar was mixed with 100 g of AC;
(8) A solution containing 100 g of a 3% NaOH solution and 50 g of tar was mixed with 100 g of AC;
(9) A solution containing 100 g of a 4% NaOH solution and 50 g of tar was mixed with 100 g of AC; and
(10) A solution containing 100 g of a 5% NaOH solution and 50 g of tar was mixed with 100 g of AC.

Results of Examination 10:

The above-described cases (1) to (5) resulted in precipitates recognized in the bottom although the resultants were mixed. The resultants in the cases (6) to (10) were in a slightly mixed state, and gelation was recognized at the bottom. Mixing methods where NaOH and tar are directly mixed with AC as in (1) to (10) above were recognized to be substantially unusable.

Discussion:

Accordingly, it was necessary to examine processed tars obtained by treating tar with NaOH solutions, in methods by which they are mixed in another NaOH solutions.

Examination 11:

First, processed tars were prepared as follows:
(1) 100 g of tar was mixed with 5 g of a 10% NaOH solution;
(2) 100 g of tar was mixed with 5 g of a 20% NaOH solution;
(3) 100 g of tar was mixed with 5 g of a 30% NaOH solution;
(4) 100 g of tar was mixed with 5 g of a 40% NaOH solution;
(5) 100 g of tar was mixed with 5 g of a 50% NaOH solution;
(6) 100 g of tar was mixed with 10 g of a 10% NaOH solution;
(7) 100 g of tar was mixed with 10 g of a 20% NaOH solution;
(8) 100 g of tar was mixed with 10 g of a 30% NaOH solution;
(9) 100 g of tar was mixed with 10 g of a 40% NaOH solution;
(10) 100 g of tar was mixed with 10 g of a 50% NaOH solution;
(11) 100 g of tar was mixed with 15 g of a 10% NaOH solution;
(12) 100 g of tar was mixed with 15 g of a 20% NaOH solution;
(13) 100 g of tar was mixed with 15 g of a 30% NaOH solution;
(14) 100 g of tar was mixed with 15 g of a 40% NaOH solution;
(15) 100 g of tar was mixed with 15 g of a 50% NaOH solution;
(16) 100 g of tar was mixed with 20 g of a 10% NaOH solution;
(17) 100 g of tar was mixed with 20 g of a 20% NaOH solution;
(18) 100 g of tar was mixed with 20 g of a 30% NaOH solution;
(19) 100 g of tar was mixed with 20 g of a 40% NaOH solution; and
(20) 100 g of tar was mixed with 20 g of a 50% NaOH solution.

The processed tars prepared in (1) to (20) above were mixed at amounts of 5%, 10%, 15%, and 20% in each of 1%, 2%, 3%, 4%, and 5% NaOH solutions, and 100 g of the resultant NaOH solutions was mixed with 100 g of AC (acrylic resin). Among examinations employing these materials, only examinations in which a dissolved state was achieved are described below:

(a) 100 g of tar was mixed with 10 g of a 50% NaOH solution (A), and then 10% (20 g) of the resultant mixture was mixed with 100 g of a 2–5% NaOH solution (B), which resulted in a dissolved state;

(b) 100 g of tar was mixed with 10–20 g of a 50% NaOH solution (A), and then 10–20% (20–40 g) of the resultant mixture was mixed with 100 g of a 2–5% NaOH solution (B), which resulted in a dissolved state;

(c) 100 g of tar was mixed with 10 g of a 50% NaOH solution (A), and then 6% (12 g) of the resultant mixture was mixed with 100 g of a 2% NaOH solution (B), which resulted in a dissolved state;

(d) 100 g of tar was mixed with 10 g of a 50% NaOH solution (A), and then 6% (12 g) of the resultant mixture was mixed with 100 g of a 2% NaOH solution (B) and 100 g of AC, which resulted in a dissolved state;

(e) 100 g of tar was mixed with 10 g of a 50% NaOH solution (A), and then 7% (14 g) of the resultant mixture was mixed with 100 g of a 2% NaOH solution (B), which resulted in a dissolved state;

(f) 100 g of tar was mixed with 10 g of a 50% NaOH solution (A), and then 7% (14 g) of the resultant mixture was mixed with 100 g of a 2% NaOH solution (B) and 100 g of AC, which resulted in a dissolved state;

(g) 100 g of tar was mixed with 10 g of a 50% NaOH solution (A), and then 8% (16 g) of the resultant mixture was mixed with 100 g of a 2% NaOH solution (B), which resulted in a dissolved state;

(h) 100 g of tar was mixed with 10 g of a 50% NaOH solution (A), and then 8% (16 g) of the resultant mixture was mixed with 100 g of a 2% NaOH solution (B) and 100 g of AC, which resulted in a dissolved state;

(i) 100 g of tar was mixed with 10 g of a 50% NaOH solution (A), and then 8% (16 g) of the resultant mixture was mixed with 100 g of a 3–5% NaOH solution (B), which resulted in a dissolved state;

j) 100 g of tar was mixed with 10 g of a 50% NaOH solution (A), and then 8% (16 g) of the resultant mixture was mixed with 100 g of a 3–5% NaOH solution (B) and 100 g of AC, which resulted in a dissolved state;

(k) 100 g of tar was mixed with 15 g of a 50% NaOH solution (A), and then 8% (16 g) of the resultant mixture was mixed with 100 g of a 3–5% NaOH solution (B), which resulted in a dissolved state; and (l) 100 g of tar was mixed with 15 g of a 50% NaOH solution (A), and then 8% (16 g) of the resultant mixture was mixed with 100 g of a 3–5% NaOH solution (B) and 100 g of AC, which resulted in a dissolved state.

Results of Examination 11:

Dissolved states was achieved by the following conditions:
(1) For treating tar with NaOH, the amount of an NaOH solution was 10% of the weight of tar and a 50% NaOH solution was used as an NaOH solution (A);
(2) A concentration of an NaOH solution (B) was 2%; and
(3) A content of the NaOH-treated tar from (A) was desired to be 8% or less.

Discussion:

It is necessary to determine a compatibility of the above-described tar treated with 50% NaOH solution (hereinafter referred to as NTA), with a substitute to aqueous nylon.

Examination 12:

A coating material was produced with use of 100 g of AC (acrylic resin), 100 g of 2% NaOH solution, 16 g of NTA, and 100 g of charcoal powder.

The produced coating material was applied to plywood plates having dimensions of 100×100×2.7 (mm) at an amount of 300 g/m². After drying, immersion tests were carried out.

Results of Examination 12:

Precipitation took place in the produced coating material, and gelation was caused after 7 days. This material was problems in use. The immersion test after 5 days gave good results.

Discussion:

The producing materials had problems in long-term stability. The acrylic resin alone has a short-term resistance to water, but cannot be expected to have a long-term resistance to water. In addition, the resin film formed from the coating material blocked effects of charcoal. Substitutes to aqueous nylon are required.

Examination 13 (Substitutes to Aqueous Nylon):

An aqueous tar solution was prepared by mixing 16 g of NTA in 100 g of a 2% NaOH solution. The tar solution was mixed with 100 g of an air-permeable acrylic resin.

TABLE 1

| Resin Type | Material Stability | Adsorption | Water Repellency | Evaluation |
|---|---|---|---|---|
| AC Type B | Semi-solidified | X | ○ | X |
| AC Type A | Solidified | — | — | — |
| AC Type D | Solidified | — | — | — |
| Water-Soluble Polyurethane | Gelled | — | — | — |

Discussion:

It is necessary to render the resin film permeable, in order to exert effects of charcoal. It is likely that one can take advantage of effects of charcoal by mixing both of an air-permeable resin and an air-impermeable resin.

Examination 14:

An aqueous tar solution was prepared by mixing 16 g of NTA in a 2% NaOH solution. 100 g of each of test solutions was mixed in this tar solution, results of which are shown in Table 2 below.

TABLE 2

| Mixed Resin | | Product Stability | Adsorption | Water Repellency | Evaluation |
|---|---|---|---|---|---|
| Acrylic H (50 g) | Silicone S (50 g) | ○ | ○ | Δ | ○ |
| Acrylic D | Silicone S | Semi-solidified | — | — | — |
| Acrylic B | Silicone S | Semi-solidified | — | — | — |
| Acrylic A | Silicone S | Semi-solidified | — | — | — |
| Acrylic W | Silicone S | Semi-solidified | — | — | — |
| Acrylic H | Silicone P | Gelled | — | — | — |
| Acrylic D | Silicone P | Gelled | — | — | — |
| Acrylic B | Silicone P | Gelled | — | — | — |
| Acrylic A | Silicone P | Gelled | — | — | — |
| Acrylic W | Silicone P | Gelled | — | — | — |
| Acrylic H | Silicone X | ○ | ○ | Δ | ○ |
| Acrylic D | Silicone X | Semi-solidified | — | — | — |
| Acrylic B | Silicone X | Semi-solidified | — | — | — |
| Acrylic A | Silicone X | Semi-solidified | — | — | — |

Examination 15:

TABLE 3

| Acrylic H | Silicone S | 2% NaOH | NTA | Charcoal Powder | Evaluation |
|---|---|---|---|---|---|
| 50 g | 50 g | 100 g | 16 g | 100 g | ○ |
| 67 g | 33 g | 100 g | 16 g | 100 g | ○ |
| 90 g | 10 g | 100 g | 16 g | 100 g | ○ |

The test materials listed in Table 3 above were applied to plywood plates having dimensions of 50×50×2.7 (mm) at an amount of 300 g/m² to provide test pieces or specimens. Ten specimens were prepared with ten plates per each material, and were subjected to evaluation in weathering tests.

Weathering tests were carried out as follows: The specimens were immersed into tap water for 30 seconds. After that, the specimens were put into a desiccator whose bottom portion was filled with water, which was placed in a thermostatic chamber at a temperature of 26±2° C. for 4 hours, followed by being placed in a circulating hot-air thermostat at a temperature of 40±2° C. for 20 hours. These procedures were repeated ten times.

Discussion:

Examinations of materials for making examinations as to the enhancement of properties of the Health Coat against termite damage and for rot-proofing, which is a subject matter of this research, were completed to allow composition of the following raw materials to be established.

(1) Tar is processed by mixing a 50% NaOH solution therein at an amount of 10% relative to the weight of tar (100 parts by weight);

(2) The processed tar at an amount of 8% (16 parts by weight) of a total amount of the processed tar prepared in (1) above is mixed in 100 parts by weight of a 2% NaOH solution;

(3) AC (acrylic resin) and Silicone S (9:1) are mixed with the product in (2) above; and (4) Charcoal powder is added into the mixture obtained from (3) above.

Examinations on Termite Damage:

Pre-examination:

(1) Materials to be Tested:

(a) New aqueous type: (10 g of AC H+5 g of Silicone S)+(15 g of 2% NaOH solution+0.23 g (5%) of NTA) +15 g of charcoal powder;

(b) New aqueous, termiticide-containing type: (10 g of AC H+5 g of Silicone S)+(15 g of 2% NaOH solution+0.23 g (5%) of NTA)+0.08 g of Hachikusan (trade name)+15 g of charcoal;

(c) New solvent-based type (alcoholic): (30 g of Health Coat)+0.15 g (5%) of NTA; and (d) Control (untreated).

(2) Testing Procedures:

(i) Plywood plates having dimensions of 28×28×9 mm were dried at 40±2° C. for 24 hours;

(ii) A specimen was prepared by applying each material to be tested onto the treated plywood plates at a coating amount of 300 g/m²;

(iii) The specimens from (ii) were dried in a dryer at 60±2° C. for 48 hours, and then conditioned in a silica-gel containing desiccator at room temperature for 24 hours; and (iv) The specimens from (iii) were placed into an open-topped container having a diameter of 110 mm, and the container was positioned in a group of *Reticulitermes speratus* termites (15 soldier termites and 150 worker termites). Wet conditions were maintained so as to prevent drying.

TABLE 4

| | a | b | c | d |
|---|---|---|---|---|
| 1st day | Termites gathered around the specimens and were active. | Active | Termites left the specimens and were active. | Active |
| 2nd day | Termites gathered around the specimens and were active. | Inactive | Termites left the specimens and were active. | Termite damage was observed. |
| 3rd day | Termites gathered around the specimens and were active. | " | Termites left the specimens and were active. | Termite damage was observed. |
| 4th day | Termites gathered around the specimens and were active. | "  " | Termites went under the specimens Active | Termite damage was observed. |
| 5th day | Termites started going under the specimens, and tunnel-shaped passages for termites were formed in side walls. | Dead termites were found. | Termites went under the specimens. Active | Termite damage was observed. |
| 6th day | Termites started going under the specimens, and tunnel-shaped passages for termites were formed in side walls. | More termites were killed | Termites went under the specimens. Active | Termite damage was observed. |
| 7th day | Termites started going under the specimens, and tunnel-shaped passages for termites were formed in side walls. | More termites were killed | Termites went under the specimens. Active | Termite damage was observed. |
| 8th day | Termites started going under the specimens, and tunnel-shaped passages for termites were formed in side walls. | More termites were killed | Termites went under the specimens. Active | Termite damage was observed. |
| 9th day | Termites started going under the specimens, and tunnel-shaped passages for termites were formed in side walls. and the soil became moldy. | More termites were killed | Termites went under the specimens. Active | Termite damage was observed. |
| 10th day | Termites started going under the specimens, and tunnel-shaped passages for termites were formed in side walls. and the soil became moldy. | More termites were killed | Termites went under the specimens. Active | Termite damage was observed. |
| 11th day | Termites started going under the specimens, and tunnel-shaped | More termites were killed | Termite damage was observed in side walls. | Termite damage was observed. |

TABLE 4-continued

| | a | b | c | d |
|---|---|---|---|---|
| | passages for termites were formed in side walls. and the soil became moldy. | | | |
| 12th day | Termites started going under the specimens, and tunnel-shaped passages for termites were formed in side walls. and termite damage was observed in side walls. | More termites were killed | — | Termite damage was observed. |
| 13th day | — | | All termites were killed. | — |

The combinations of AC (acrylic resin) and aqueous silicone as substitutes to an aqueous nylon solution were not capable of making effects of charcoal reach its full potential. In order to exert termite-controlling effects to a greater extent, examinations were made to redetermine the ability of a wood-vinegar solution and an essential oil of Japanese cypress leaves to control termites, which did not give good results in field tests.

Wood specimens to be subjected to the following termite-controlling tests were wood pieces defined by the Japan Wood Preserving Association, lo which were employed to carry out the testing.

(1) Wood Specimens to be Tested:
   (i) Wood specimens to be tested were sapwoods of normal Japanese black pine (*Pinus thunbergii*) or red pine (*Pinus densiflora*) and had 3 to 5 annual-growth rings in every 10 mm lengths. The specimens had 2 opposing edge-grained surfaces and every surfaces smoothly and accurately finished with a plane. The wood specimens were rectangular parallelepipeds having dimensions of 20±0.5 mm length×10±0.5 mm width×10±0.5 mm height.
   (ii) The wood specimens were dried in a thermostat dryer at a temperature of 60±2° C. for 24 hours.

(2) Test Specimen:
   (i) Of 10 specimens onto which a material to be tested was applied, 5 specimens were subjected to a weathering process before testing them.
   (ii) The weathering process consisted of ten cycles of a wetting process and a vaporizing process by alternation.
   (iii) Weathering Procedures: Specimens were immersed into still water at room temperature for 30 seconds, and then put into a desiccator, whose bottom portion was filled with water, which in turn was placed in a thermostatic chamber at a temperature of 26±2° C. for 4 hours. immediately after that, the desiccator was placed in a circulating hot air thermostat at a temperature of 40±2° C. for 20 hours.

(3) Testing Procedures:

Each test specimen was put into a group of 150 worker termites and 15 soldier termites, which was kept in the dark at a temperature of 28±2° C. to observe changes over time.

Examination 16:

The following materials were examined:
(i) an essential oil of Japanese cypress leaves;
(ii) a wood-vinegar solution; and
(iii) a mixture of an essential oil of Japanese cypress leaves and a wood-vinegar solution (1:1).

TABLE 5

| Days | Material (i) | Material (i) with Weathering Process | Material (ii) | Material (ii) with Weathering Process | Material (iii) | Material (iii) with Weathering Process |
|---|---|---|---|---|---|---|
| 1 | No termite damage | No termite damage | No termite damage | No termite damage | No termite damage | No termite damage |
| 2 | No termite damage | No termite damage | Termite damage was observed. | Termite damage was observed. | No termite damage | No termite damage |
| 3 | No termite damage | No termite damage | — | — | No termite damage | No termite damage |
| 4 | No termite damage | No termite damage | — | — | No termite damage | No termite damage |
| 5 | No termite damage | Termite damage was observed | — | — | No termite damage | Termite damage was observed |
| 6 | No termite damage | — | — | — | No termite damage | — |
| 7 | No termite damage | — | — | — | No termite damage | — |
| 8 | No termite damage | — | — | — | Termite damage was observed | — |
| 9 | No termite damage | — | — | — | — | — |
| 10 | No termite damage | — | — | — | — | — |
| 11 | No termite damage | — | — | — | — | — |
| 12 | No termite damage | — | — | — | — | — |
| 13 | No termite damage | — | — | — | — | — |
| 14 | No termite damage | — | — | — | — | — |
| 15 | No termite damage | — | — | — | — | — |

Discussion:

The specimens for the essential oil of Japanese cypress leaves which were subjected to the weathering process did not undergo termite damage in a period of 15 days, whereas the specimens which were subjected to the weathering process underwent termite damage. The capability was retained only in a period of 1 to 1.5 years in field tests. It is regarded that the use of wood vinegar and an essential oil of Japanese cypress leaves is not effective.

The combinations of AC (acrylic resin) and aqueous silicone as a substitute to an aqueous nylon solution were not capable of making effects of charcoal reach its full potential, but they are resins which can be used. Although adsorptive capability may be decreased, it is necessary to contain zeolite, among natural materials, and to determine its effect as methods for enhancing adsorptive capability, since it will be advantageous if capabilities of adsorption and controlling termites can be enhanced to a moderate degree.

Examination 17:

The following materials were examined:
(i) 90 g of AC H+10 g of Silicone S+100 g of 2% NaOH solution+16 g of NTA+160 g of charcoal powder+80 g of zeolite;
(ii) 90 g of AC H+10 g of Silicone S+100 g of 2% NaOH solution+16 g of NTA+80 g of charcoal powder+80 g of zeolite; and
(iii) 90 g of AC H+10 g of Silicone S+100 g of 2% NaOH solution+16 g of NTA+80 g of charcoal powder+160 g of zeolite.

TABLE 6

| Days | Material (i) | Material (ii) | Material (iii) |
|---|---|---|---|
| 1 | Active | Active | |
| 2 | " | " | |
| 3 | " | " | |
| 4 | " | " | 70% of the termites were killed. |
| 5 | " | " | 70% of the termites were killed. |
| 6 | " | " | 70% of the termites were killed. |

TABLE 6-continued

| Days | Material (i) | Material (ii) | Material (iii) |
|------|--------------|---------------|----------------|
| 7    | "            | "             | —              |
| 8    | "            | "             | —              |
| 9    | "            | "             | —              |
| 10   | "            | "             | —              |

Discussion:

It was observed that increasing amounts of zeolite had an effect of killing termites.

Examination 18:

The following materials were examined:
(i) 90 g of AC H+10 g of Silicone S+50 g of zeolite; and
(ii) 90 g of AC H+10 g of Silicone S+100 g of 2% NaOH solution+100 g of NTA+100 g of zeolite.

Results of Examination 18:

Both above-described materials (i) and (ii) resulted in the precipitation of the zeolite and thus were incapable of application.

Examination 19:

The following materials were examined:
(i) 90 g of AC H+10 g of Silicone S+40 g of zeolite+10 g of charcoal powder;
(ii) 90 g of AC H+10 g of Silicone S+30 g of zeolite+20 g of charcoal powder;
(iii) 90 g of AC H+10 g of Silicone S+100 g of 2% NaOH solution+16 g of NTA+80 g of zeolite+20 g of charcoal powder; and
(iv) 90 g of AC H+10 g of Silicone S+100 g of 2% NaOH solution+16 g of NTA+60 g of zeolite+40 g of charcoal powder.

Results of Examination 19:

All the above-described materials (i) to (iv) were mixed well and had a good stability.

Discussion:

Charcoal powder was absolutely required for dispersing zeolite. It is necessary to determine the ratio of zeolite and charcoal powder.

Examination 20:

The following materials (i) to (iv) were mixed in solutions of 90 g of AC H and 10 g of Silicone S:
(i) 45 g of zeolite+5 g of charcoal powder→poorly dispersible;
(ii) 40 g of zeolite+10 g of charcoal powder→dispersible;
(iii) 35 g of zeolite+15 g of charcoal powder→dispersible; and
(iv) 30 g of zeolite+20 g of charcoal powder→dispersible.

Discussion:

Charcoal powder was required at an amount of 10% of the total resin amount, in order to achieve the dispersibility of the mixed zeolite. Capabilities of charcoal include an effect of making organisms get better, and it is likely that charcoal may permit even termites to become active. By mixing zeolite, the ability to kill termites was ascertained from the results of the above-described Examination 17. Although the ability to kill termites are not provided by charcoal alone, it was ascertained that effects of repellency, killing termites, conditioning the humidity, deodorizing, and the like can be exerted by synergistic effects of NTA, zeolite, and charcoal powder.

Examination 21:

In the bottom of a given container, three filter papers were laid, onto which were placed one of test specimens which were subjected to the weathering treatment:
(i) 90g of AC H+10 g of Silicone S+100 g of 2% NaOH solution+16 g of NTA;
(ii) 90 g of AC H+10 g of Silicone S+100 g of 2% NaOH solution+16 g of NTA+12 g of charcoal powder;
(iii) 100 g of Health Coat (alcoholic)+8 g of tar;
(iv) 90 g of AC H+10 g of Silicone S+100 g of 2% NaOH solution+16 g of NTA+20 g of charcoal powder+60 g of zeolite; and
(v) 90 g of AC H+10g of Silicone S+100 g of 2% NaOH solution+6 g of NTA+20 g of charcoal powder+60 g of zeolite.

TABLE 7

| Days | Test Specimen (i) | Test Specimen (ii) | Test Specimen (iii) | Test Specimen (iv) | Test Specimen (v) |
|------|-------------------|--------------------|--------------------|--------------------|-------------------|
| 1 | Termites left the test specimen | Active | Active | 80% of the termites (*Coptotermes formosanus*) were killed | Active |
| 2 | Termites left the test specimen | " | " | 80% of the termites (*Coptotermes formosanus*) were killed | " |
| 3 | Termites left the test specimen | " | " | 80% of the termites (*Coptotermes formosanus*) were killed | " |
| 4 | Termites left the test | " | " | 80% of the termites | " |

TABLE 7-continued

| Days | Test Specimen (i) | Test Specimen (ii) | Test Specimen (iii) | Test Specimen (iv) | Test Specimen (v) |
|---|---|---|---|---|---|
| | specimen | | | (*Coptotermes formosanus*) were killed | |
| 5 | Termites left the test specimen | " | " | 100% of the termites (*Coptotermes formosanus*) were killed | " |
| 6 | Termites left the test specimen | " | " | — | " |
| 7 | Termites left the test specimen | " | " | — | " |
| 8 | Termites left the test specimen | " | " | — | " |
| 9 | Termites left the test specimen | " | " | — | " |
| 10 | Termites left the test specimen | " | " | — | " |
| 11 | Termites went under the filter papers and left the test specimen | " | " | Re-examination was made with *Reticulitermes speratus* termites | " |
| 12 | Termites went under the filter papers and left the test specimen | " | " | — | " |
| 13 | Termites went under the filter papers and left the test specimen | Termites went under the filter papers Active; Active even on the surfaces of the test specimen | " | Termites got weakened slightly | " |
| 14 | Termites begun to get weakened slightly and went under the filter papers | Termites went under the filter papers Active; Active even on the surfaces of the test specimen | " | Termites got weakened | " |
| 15 | Termites begun to get weakened slightly and went under the filter papers | Termites went under the filter papers Active; Active even on the surfaces of the test specimen | " | 50% of the termites were killed | " |
| 16 | Termites begun to get weakened slightly and went under the filter papers | Termites went under the filter papers Active; Active even on the surfaces of the test specimen | " | 80% of the termites were killed | " |
| 17 | Termites begun to get weakened slightly and went under the filter papers | Termites went under the filter papers Active; Active even on the surfaces of the test specimen | " | 2 termites were alive | " |
| 18 | Termites begun to get weakened | Termites went under the filter papers | | 2 termites were alive | |

TABLE 7-continued

| Days | Test Specimen (i) | Test Specimen (ii) | Test Specimen (iii) | Test Specimen (iv) | Test Specimen (v) |
|---|---|---|---|---|---|
| | slightly and went under the filter papers | Active; Active even on the surfaces of the test specimen | | | |
| 19 | Termites begun to get weakened slightly and went under the filter papers | Termites went under the filter papers Active; Active even on the surfaces of the test specimen | " | — | " |
| 20 | Termites begun to get weakened slightly and went under the filter papers | Termites went under the filter papers Active; Active even on the surfaces of the test specimen | " | — | " |
| 21 | Termites begun to get weakened slightly and went under the filter papers | Termites went under the filter papers Active; Active even on the surfaces of the test specimen | " | — | " |
| 22 | Termites begun to get weakened slightly and went under the filter papers | Termites went under the filter papers Active; Active even on the surfaces of the test specimen | " | — | " |
| 23 | Termites begun to get weakened slightly and went under the filter papers | Termites went under the filter papers Active; Active even on the surfaces of the test specimen | " | — | " |
| 24 | Termites begun to get weakened slightly and went under the filter papers | Termites went under the filter papers Active; Active even on the surfaces of the test specimen | " | — | " |
| 25 | Termites begun to get weakened slightly and went under the filter papers | Termites went under the filter papers Active; Active even on the surfaces of the test specimen | " | — | " |
| 26 | Termites begun to get weakened slightly and went under the filter papers | Termites went under the filter papers Active; Active even on the surfaces of the test specimen | " | — | " |
| 27 | Termites begun to get weakened slightly and went under the filter | Termites went under the filter papers Active; Active even on the surfaces of | " | — | " |

TABLE 7-continued

| Test Days | Test Specimen (i) | Test Specimen (ii) | Test Specimen (iii) | Test Specimen (iv) | Test Specimen (v) |
|---|---|---|---|---|---|
| | papers | the test specimen | | | |
| 28 | Termites begun to get weakened slightly and went under the filter papers | Termites went under the filter papers Active; Active even on the surfaces of the test specimen | " | — | " |
| 29 | Termites begun to get weakened slightly and went under the filter papers | Termites went under the filter papers Active; Active even on the surfaces of the test specimen | " | — | " |
| 30 | No termite damage | Termites went under the filter papers Active; Active even on the surfaces of the test specimen | " | — | " |

Discussion:

In the test specimen (i), it was possible to ascertain that tar has a termite-repellent effect. In the test specimen (iii), charcoal has an capability of making organisms get better, and permitted even termites to become active. For enhancing the effect of controlling termites, it is necessary to reduce the amount of charcoal powder and contain zeolite and tar, whereby the effect of killing termites was ascertained. The amount ratio of charcoal powder, zeolite, and tar to be mixed was allowed to be established.

Examination 22:

Culture examinations were made by placing agar medium into testing containers for culturing fungi and applying the following materials (i) and (ii) onto sterilized glass plates. After the glass plates were set in the containers, the tops of the containers were removed from the containers for 60 seconds and put back on the containers, and placed into a desiccator whose bottom was filled with water. The desiccator was put into a thermostatic chamber at a temperature of 26±2° C. to observe the incidence of colonies after 48 hours.

(i) 90 g of AC H+10 g of Silicone S+16 g of NTA+100 g of 2% NaOH solution; and (ii) 90 g of AC H+10 g of Silicone S+100 g of 2% NaOH solution+16 g of NTA+20 g of charcoal powder+60 g of zeolite.

TABLE 8

| Material (i) | Material (ii) | Control |
|---|---|---|
| − | − | +++ |

* The materials (i) and (ii) did not result in the formation of colonies.

Discussion:

(1) NTA was ascertained to have a rot proofing (antifungal) property.

(2) Charcoal allows the growth of various microorganisms, but mixing of NTA therein was observed to provide a rot proofing (antifungal) effect.

Examination 23:

Drying tests to a resin coating composition with tar mixed were carried out.

Testing Procedures:

(i) 60 g of tar was mixed with 6 g of a 50% NaOH solution to prepare a processed tar. The processed tar was mixed in 1000 g of a 2% NaOH aqueous solution to prepare an aqueous tar solution. The aqueous tar solution was mixed with 900 g of an acrylic resin, 100 g of a silicone resin, 600 g of zeolite, and 200 g of charcoal powder to produce an aqueous coating composition.

The aqueous coating composition thus produced was applied onto glass plates having dimensions of 200 mm×200 mm at amounts of 4 g (100 g/m$^2$), 8 g (200 g/m$^2$), and 12 g (300 g/m$^2$), respectively.

(ii) Time periods of drying to the touch were determined for each of the specimens produced in (i) above, in a moisture of 65% and at a temperature of 25° C.

(iii) Time periods of complete drying were determined for each of the specimens produced in (i) above, in a moisture of 65% and at a temperature of 25° C.

TABLE 9

| | drying to the touch | complete drying |
|---|---|---|
| 4 g | about 35 minutes | about 1 hour and 30 minutes |
| 8 g | about 35 minutes | about 1 hour and 30 minutes |
| 12 g | about 35 minutes | about 1 hour and 30 minutes |

Discussion:

Generally, although tar can be almost uniformly mixed in a solvent medium, while the solvent medium vaporizes, the tar remains in a tacky state so that we cannot touch it without being soiled. However, it was confirmed that tar was able to be changed from lipophilic to hydrophilic by processing the tar with an NaOH solution of a determined concentration. Further, it was confirmed that the processed tar was able to be made into a colorfast, room temperature-setting composition by mixing the processed tar with a resin, charcoal powder, and zeolite.

Conclusions:

Although it has been known that tar, among natural materials, had insect-repellent and rot-proof effects, tar has not been used so much, since tar has problems in its stability during preservation and in that tar cannot be dried. However, the present invention enables tar to be used as a tar-containing coating composition by processing the tar. In addition, while zeolite alone has simply an adsorptive effect within the limits of its physical capabilities, zeolite is imparted with synergy effects to provide termite-repellent and termite-killing effects by mixing the zeolite with the processed tar and charcoal powder. Moreover, new products taking advantage of charcoal effects can be produced according to the present invention.

INDUSTRIAL APPLICABILITY

As described above, the aqueous tar solution according to the present invention can be obtained by mixing and dissolving tar and an NaOH solution, whereby the tar can be dissolved in a liquid in a stable state, resulting in the formation of an aqueous tar solution that does not cause disadvantages such as precipitation, separation, and the like, and exerts superior effects of enhancing properties against termite damage and for rot-proofing.

In addition, the tar-containing coating composition according to the present invention not only can be applied onto lumbers and others with good dispersibility by mixing a tar aqueous solution having tar and an NaOH solution mixed and dissolved therein into an aqueous coating composition having resin as the major component and containing charcoal powder, thereby dissolving tar in the aqueous coating composition, but also possess rot- and termite-proofing effects. The tar-containing coating composition of the present invention does not make human bodies and the environment dirty and also can be expected to have effect of charcoal on humidity conditioning and deodorizing. Furthermore, since an applied tar is dried, the tar-containing coating composition of the present invention exerts various superior effects of not resulting in any soil caused by attaching in surrounding areas.

The invention claimed is:

1. A wood-based tar-containing coating composition comprising:
   100 parts by weight of an acrylic resin, or a mixture of 50 to 90 parts by weight of the acrylic resin and 50 to 10 parts by weight of a silicone resin;
   10 to 20 parts by weight of a processed tar which is prepared by mixing 100 parts by weight of a wood-based tar with 10 to 50 parts by weight of a 10–50% NaOH solution;
   100 parts by weight of a 2–5% NaGH solution;
   10 to 20 parts by weight of charcoal powder; and
   30 to 60 parts by weight of zeolite.

* * * * *